United States Patent [19]

Sondermeijer et al.

[11] Patent Number: 5,554,525

[45] Date of Patent: Sep. 10, 1996

[54] CHICKEN ANEMIA VIRUS VACCINE AND DIAGNOSTIC

[75] Inventors: Paulus J. A. Sondermeijer; Johannes A. J. Claessens, both of Boxmeer, Netherlands

[73] Assignee: Akzo Nobel N.V., Arnhem, Netherlands

[21] Appl. No.: 917,722

[22] Filed: Jul. 20, 1992

Related U.S. Application Data

[63] Continuation of Ser. No. 605,881, Oct. 31, 1990, abandoned.

[51] Int. Cl.$^6$ .............................. C12N 15/34; C12N 7/01; C12N 1/21; C12N 5/10
[52] U.S. Cl. ................................ 435/240.1; 536/23.72; 435/252.3; 435/254.11; 435/320.1; 435/235.1; 935/12
[58] Field of Search ................................. 536/27, 23.72; 435/320.1, 252.3, 69.1, 235.1, 240.1, 254.11; 424/89; 935/12

[56] References Cited

U.S. PATENT DOCUMENTS 5,491,073  2/1996  Noteborn et al. ..................... 435/69.1

FOREIGN PATENT DOCUMENTS 0431668  11/1990  European Pat. Off. ......... C12N 15/86
8802026   3/1988  WIPO ............................. C12N 15/00

OTHER PUBLICATIONS

N. Yuasa et al., "Survey of Antibody Against Chicken Anaemia Agent (CAA) by an Indirect Immunofluorescent Antibody Technique in Breeder Flocks in Japan," Avian Pathology, vol. 14, pp. 521–530, 1985.
Ozawa, K. et al. 1987. Journal of Virology, vol. 61, p. 2395–2406.
Parker, M. D. et al. 1989. J. Gen. Virol. vol. 70 p. 155–164.
De Groot, R. J. et al. 1987. J. Gen. Virol. vol. 68 p. 2639–2646.
Azad, A. A. et al. 1985. Virology vol. 143 p. 135–144.
Davis, V. S. et al. 1990. Avian Diseases vol. 34 p. 329–335.
McFarlane, R. G. et al. 1990. J. Virol. Meth. vol. 27 p. 175–188.
Hanold, D. et al. 1988. J. Gen. Virol. vol. 69 p. 1323–1329.
Rhode, W. et al. 1990. Virology vol. 176 p. 648–651.
Anderson, M. T. et al. 1988. Virology vol. 164 p. 443–449.
Young, R. A. et al. (83) Proc. Natl. Acad. Sci. USA 80:1194–1198.
Helfman, D. M. et al. (87) Meth. Enzym. 152:451–457.
Mierendorf, R. C. et al. (87) Meth. Enzym. 152:458–469.
Finkelstein, A. et al. (89) Trends in Biotech. 7:273–277.
Todd, D. et al. (1990a) J. Gen Virol. 71:819–823.
Todd, D. et al. (1990b) Avian Dis.34:359–363.
McNulty, M. S. et al. (90) Avian Dis. 34:352–358.
Todd, D. et al. (1991) J. Clin. Microbiol. 29:933–939.
Noteborn, M. H. M. et al. (1991) J. Virol. 65:3131–3139.

*Primary Examiner*—Mary E. Mosher
*Attorney, Agent, or Firm*—Mary E. Gormley

[57] ABSTRACT

The invention is related to a nucleic acid sequence containing the genetic information of the chicken anemia virus (CAV). Especially, three genomic regions are identified encoding viral polypeptides. Said regions or polypeptides can be used for the preparation of a vaccine against CAV infection or for diagnostic purposes. The invention is also concerned with a test kit useful for the detection of CAV infected chickens.

9 Claims, 5 Drawing Sheets

HVT HOMOLOGOUS REGION

CHICKEN ANEMIA VIRUS VACCINE AND DIAGNOSTIC

This is a continuation of application Ser. No. 07/605,881 filed Oct. 31, 1990 now abandoned.

The present invention is concerned with a nucleic acid sequence encoding a chicken anemia virus related polypeptide, a recombinant nucleic acid molecule comprising such a nucleic acid sequence, a vector virus containing said nucleic acid sequence, a host cell transformed with such a nucleic acid sequence, a chicken anemia virus related polypeptide and antibodies reactive therewith, a chicken anemia virus mutant as well as a vaccine against chicken anemia virus infection.

The invention also relates to an immunochemical reagent and a test kit comprising said reagent.

BACKGROUND OF THE INVENTION

The chicken anemia virus (CAV) causes infectious anemia in chickens. While CAV apparently can infect birds of all ages, signs of illness only have been reported in young birds. CAV's are also immunosuppressive. In normal healthy birds the thymus is responsible for the production of T-cells in young birds, the bursa of Fabricius produces B-cells and the bone marrow produces white blood cells in addition to red blood cells. When chicks are infected with CAV, destruction of said cells mentioned above occurs. Depression, anemia and immunosuppression occur within 7-14 days. Especially, chicks up to several weeks of age display severe signs of anemia and immunosuppression. Mortality rates in naturally-infected chicken flocks are usually up to 30% and recovery of the survivors usually becomes complete by 24-32 days post-infection.

Secondary infections, especially viral and bacterial infections, are common and enhance the symptoms caused by CAV raising the mortality rates in these instances well over 30%. Older birds may become infected but do not develop disease, although sub-clinical signs are considered to be the cause of a decline of the performance of the chickens.

Serological evidence indicates that in over 90% of tested chicken breeder flocks circulating CAV antibodies are present one time or another and hence were infected with the virus. The ubiquitous nature of CAV has well been reported.

SUMMARY OF THE INVENTION

Apparently, CAV can be transmitted horizontally and vertically (from dam to chick in ovo). The virus particles are very stable and are not destroyed by a variety of chemicals, e.g. chloroform or by heating to 60° C. for 30 minutes. The CAV has been described to be a naked, spherical virus with a diameter of about 24 nm and contains a circular, single-stranded DNA genome of about 2300 bp.

The ubiquitous nature of CAV combined with the mortality rates at young age and the decline of performance of older chickens, is the cause of a need for a safe and efficacious vaccine to prevent CAV infection or disease.

Conventional vaccines comprise chemically inactivated virus vaccines or modified live-virus vaccines. However, inactivated vaccines require additional immunizations, disadvantageously contain adjuvants, are expensive to produce and are laborious to administer. Further, some infectious virus particles may survive the inactivation process and may cause disease after administration to the animal.

In general, attenuated live virus vaccines are preferred because they evoke an immune response often based on both humoral and cellular reactions. Up to now, such vaccines based on CAV strains can only be prepared by serial passage of virulent strains in tissue culture. However, because of this treatment uncontrolled mutations are introduced into the viral genome, resulting in a population of virus particles heterogeneous in their virulence and immunizing properties. In addition it is well known that such traditional attenuated live virus vaccines can revert to virulence resulting in disease of the inoculated animals and the possible spread of the pathogen to other animals. Improved vaccines might be constructed based on recombinant DNA technology which only contain the necessary and relevant CAV immunogenic material which is capable of eliciting an immune response against the CAV pathogens, or the genetic information encoding said material, and do not display above-mentioned disadvantages of the live or inactivated vaccines.

According to the present invention a nucleic acid sequence encoding a CAV related polypeptide is provided which can be applied for the preparation of a vaccine for the immunization of poultry against CAV and for the preparation of a diagnostic test.

"Nucleic acid sequence" as used herein refers to a polymeric form of nucleotides of any length, both to ribonucleic acid sequences and to deoxyribonucleic acid sequences. In principle, this term refers to the primary structure of the molecule. Thus, this term includes double and single stranded DNA, as well as double and single stranded RNA, and modifications thereof.

In general, the term "polypeptide" refers to a molecular chain of amino acids with a biological activity, does not refer to a specific length of the product and if required can be modified in vivo or in vitro, for example by glycosylation, amidation, carboxylation or phosphorylation; thus inter alia, peptides, oligopeptides and proteins are included.

In particular, according to the invention three nucleic acid sequences containing a region encoding the CAV related polypeptides designated ORF 1-3, respectively, have been identified and characterized.

Figure 2:
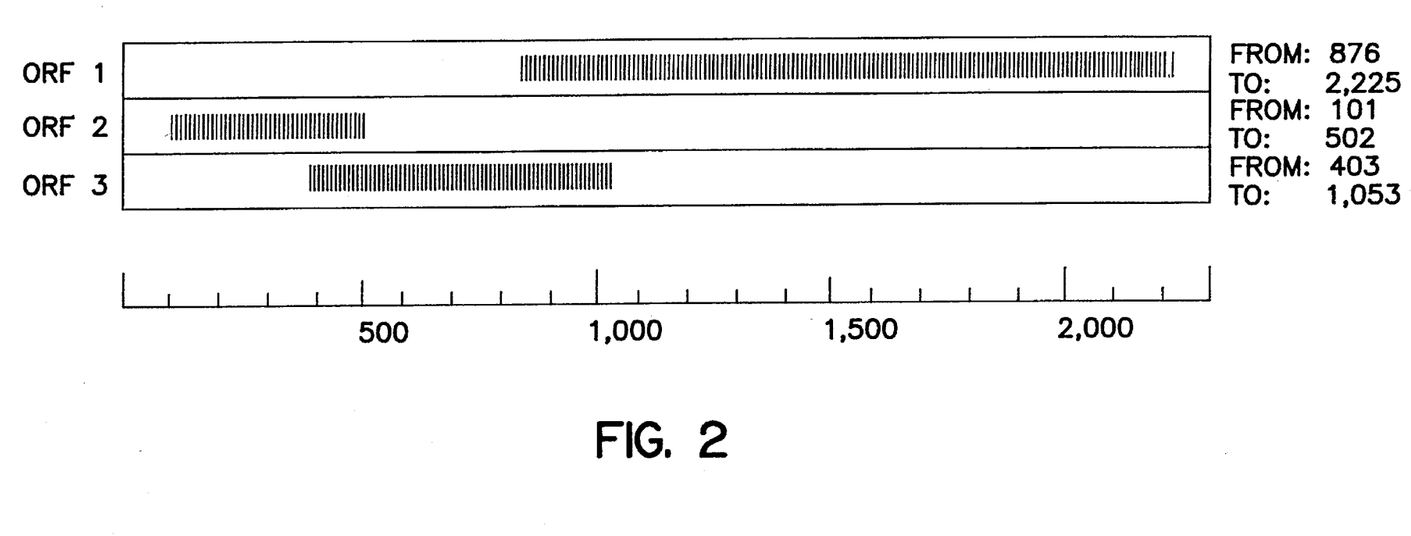

The region encoding the ORF-1 polypeptide maps from nucleotides 876 to 2225 (SEQ ID NO: 1, FIG. 2) and encodes a polypeptide of about 449 amino acids in length. The amino acid sequence of the polypeptide encoded by the ORF-1 gene is shown in SEQ ID NO: 2. Some sequence heterogeneity was detected at nucleotides 1657 and 2185. These sequence variations result in conservative amino acid changes and therefore are not considered to significantly affect the biological activity of the polypeptide.

The region encoding the ORF-2 polypeptide maps from nucleotides 101 to 502 (SEQ ID NO: 1, FIG. 2) on a second reading frame of the genome and encodes a polypeptide of about 133 amino acids in length. The amino acid sequence of the polypeptide encoded by the ORF-2 gene is shown in SEQ ID NO: 3.

The region encoding the ORF-3 polypeptide maps from nucleotides 403 to 1053 (SEQ ID NO: 1, FIG. 2) on a third reading frame of the genome and encodes a polypeptide of about 216 amino acids in length. The amino acid sequence of the polypeptide encoded by the ORF-3 gene is shown in SEQ ID NO: 4.

Therefore, this invention provides a nucleic acid sequence that encodes the ORF-1 polypeptide, ORF-2 polypeptide or ORF-3 polypeptide having an amino acid sequence shown in SEQ ID NO: 2, SEQ ID NO: 3, or SEQ ID NO: 4, respectively.

DETAILED DESCRIPTION OF THE INVENTION

As known in the art, usually not every part of the genome is represented in the mature mRNA that is translated. Mature biologically functional proteins can be added up from fragments of several ORFs in vivo by way of RNA splicing. An example of the modifications that are possible at the RNA level before mature mRNA is ready for translation, is the processing of RNA transcripts in Parvoviridea. As reviewed by Berns et al., (J. Gen. Virol. 68, 601–614, 1987) Parvoviridea are comparable to CAV in their constitution, being very small, non-enveloped, single stranded DNA viruses. RNA processing is required to assemble the parvoviral coat-proteins and non-structural proteins that are each encoded from several ORFs in several translational frames.

To make a map of the transcribed regions of the genome several techniques are used routinely (described in Maniatis et al., Molecular Cloning, A laboratory Manual, Cold Spring Harbor Laboratory Press, U.S.A., 1989), for instance: making cDNA of isolated CAV mRNA, performing in vitro CAV mRNA translations, and several ways of transcript mapping, like S1 nuclease-protection assays and primer extension analyses.

These techniques enable the construction of a transcription map of the CAV genome, and give an idea of the relative abundance of the transcripts. This way the actual genes can be located that encode the CAV related polypeptides.

Hence, also a nucleic acid sequence comprising nucleotide sequences derived from different ORFs is within the scope of the present invention.

Also included within the scope of the present invention are nucleic acid sequences encoding a functional equivalent of said ORF-1, ORF-2 or ORF-3 polypeptide having corresponding immunological characteristics.

It will be understood that for the particular ORF 1–3 polypeptides embraced herein, derived from the 26P4 CAV strain, natural variations can exist between individual viruses or strains of chicken anemia viruses. These variations may be demonstrated by (an) amino acid difference(s) in the overall sequence or by deletions, substitutions, insertions, inversions or additions of (an) amino acid(s) in said sequence. Amino acid substitutions from which can be expected that they do not essentially alter biological and immunological activities, have been described. Amino acid replacements between related amino acids or replacements which have occurred frequently in evolution are, inter alia Ser/Ala, Ser/Gly, Asp/Gly, Asp/Asn, Ile/Val (see Dayhof, M.D., Atlas of protein sequence and structure, Nat. Biomed. Res. Found., Washington D.C., 1978, vol. 5, suppl. 3). Based on this information Lipman and Pearson developed a method for rapid and sensitive protein comparison (Science 227, 1435–1441, 1985) and determining the functional similarity between homologous polypeptides. Nucleic acid sequences encoding such homologous functional equivalents are included within the scope of this invention. Moreover, the potential exists to use recombinant DNA technology for the preparation of nucleic acid sequences encoding these various functional equivalents.

Nucleic acid sequences according to the invention may be derived from isolates of CAV strains such as Cuxhaven-1, TK-5803 or Gifu-1.

The information provided in SEQ ID NO: 1–4 allows a person skilled in the art to isolate and identify the nucleic acid sequences encoding the variant functional equivalent polypeptides mentioned above having corresponding immunological characteristics with the ORF 1–3 polypeptides disclosed herein. The generally applied Southern Blotting technique or colony hybridization can be used for that purpose (Experiments in Molecular Biology, ed. R. J. Slater, Clifton, U.S.A., 1986; Singer-Sam, J. et al., Proc. Natl. Acad. Sci. 80, 802–806, 1983; Maniatis T. et al., Molecular Cloning, A laboratory Manual, Cold Spring Harbor Laboratory Press, USA, 1989). For example, restriction enzyme digested DNA derived from a specific CAV strain is electrophoresed and transferred, or "blotted" thereafter onto a piece of nitrocellulose filter. It is now possible to identify CAV related sequences on the filter by hybridization to a defined labeled DNA fragment or "probe" a synthetic oligonucleotide containing a sequence deduced from the amino acid sequences shown in SEQ ID NO: 2–4, under specific conditions of salt concentration and temperature that allow hybridization of the probe to homologous DNA sequences present on the filter. After washing the filter, hybridized material may be detected by autoradiography. The corresponding DNA restriction fragment can now be eluted from an agarose gel and used to direct the synthesis of a polypeptide functionally equivalent to a polypeptide disclosed in SEQ ID NO: 2–4.

For example, pCA1, pCA3 or a fragment thereof is expected to contain a highly conserved sequence structure, as compared to the genome of other strains of CAV, and is used in hybridization experiments. In this way quantitative, and qualitative information is obtained on the CAV infection status of an animal or of specific materials. The samples to be examined are blood (particularly lymphocytes), organ material (e.g. liver, kidney), embryo-homogenate, or MDCC-MSB1 cells (Akiyama et al., Biken J. 17, 105–117, 1974) incubated with one of these samples. A crude DNA preparation is made according to standard protocols (Berger and Kimmel, eds., Methods in Enzymology 152, 181, 1987). A serial dilution of each sample is blotted onto nitrocellulose membranes, and probed with labeled pCA1, pCA3 or fragments thereof (Maniatis et al., 1989, ibid). After detection, signals are quantified by comparison to the signals obtained from a serial dilution of a standard amount of CAV DNA in the same experiment. Negative samples are those that give no (detectable) signal, with detection limit usually at less then 2 pmoles of CAV DNA per ml.

In another way CAV related DNA may be cloned into a λgt11 phage and expressed into a bacterial host. Recombinant phages can then be screened with polyclonal serum raised against the purified ORF 1–3 polypeptides, determining the presence of corresponding immunological regions of the variant polypeptide. The production of the polyclonal serum to be used herein elicited against ORF 1–3 is described below.

As is well known in the art, the degeneracy of the genetic code permits substitution of bases in a codon resulting in another codon but still coding for the same amino acid, e.g. the codon for the amino acid glutamic acid is both GAT and GAA. Consequently, it is clear that for the expression of a polypeptide with the amino acid sequence shown in SEQ ID NO: 2–4 use can be made of a derivate nucleic acid sequence (functional equivalent) with such an alternative codon composition different from the nucleic acid sequence shown in said SEQ ID's.

According to the present invention a nucleic acid sequence is provided comprising the CAV genome or a fragment thereof.

A preferred nucleic acid sequence according to the invention is characterized in that said sequence contains at least part of the deoxyribonucleic acid sequence shown in SEQ ID NO: 1.

Particular useful fragments of said deoxy ribonucleic acid sequence are those encoding a polypeptide.

Especially, a nucleic acid sequence comprising at least part of the ORF located at the CAV genome positions 876 to 2225, 101 to 502 or 403 to 1053 shown in SEQ ID NO: 1 is incorporated into the present invention.

In addition, the nucleotides located at the position 2230 to 2298 in the viral genome attached to nucleotides 1 to 870 contain sequences that can be used for controlling the expression of heterologous genes placed under control of said sequences.

Furthermore, also fragments of the nucleic acid sequences encoding the ORF 1–3 polypeptides or functional equivalents thereof as mentioned above are included in the present invention.

The term "fragment" as used herein means a DNA or amino acid sequence comprising a subsequence of one of the nucleic acid sequences or polypeptides of the invention. Said fragment is or encodes a polypeptide having one or more immunoreactive and/or antigenic determinants of a CAV related polypeptide, i.e. has one or more epitopes which are capable of eliciting an immune response in a chicken and/or is capable of specifically binding to a complementary antibody. Methods for determining usable polypeptide fragments are outlined below. Fragments can inter alia be produced by enzymatic cleavage of precursor molecules, using restriction endonucleases for the DNA and proteases for the polypeptides. Other methods include chemical synthesis of the fragments or the expression of polypeptide fragments by DNA fragments.

All modifications resulting in such functional equivalents of the ORF 1–3 polypeptides are included within the scope of the present invention for as long as the immunological characteristics of the ORF-1, ORF-2 or ORF-3 polypeptide remain unaffected in essence.

A nucleic acid sequence according to the invention also comprises a nucleic acid sequence synthesized in vitro or obtained via for instance PCR technology.

A nucleic acid sequence according to the present invention can be ligated to various replication effecting DNA sequences with which it is not associated or linked in nature, optionally containing portions of DNA encoding fusion protein sequences such as β-galactosidase, resulting in a recombinant nucleic acid molecule which can be used for the transformation of a suitable host. Such hybrid DNA molecules are preferably derived from, for example plasmids, or from nucleic acid sequences present in bacteriophages, cosmids or viruses. Specific vectors which can be used to clone nucleic acid sequences according to the invention are known in the art and include inter alia plasmid vectors such as pBR322, the various pUC, pGEM and Bluescript plasmids, bacterio-phages, e.g. λgt-Wes-λ B, Charon 28 and the M13 derived phages or viral vectors such as SV40, adenovirus or polyoma virus (see also Rodriquez, R. L. and D. T. Denhardt, ed., Vectors: A survey of molecular cloning vectors and their uses, Butterworths, 1988; Lenstra, J. A. et al., Arch. Virol. 110, 1–24, 1990). The methods to be used for the construction of a recombinant nucleic acid molecule according to the invention are known to those of ordinary skill in the art and are inter alia forth in Maniatis, T. et al. (Molecular Cloning A Laboratory Manual; Cold Spring Harbor Laboratory, 1982). For example, the insertion of the nucleic acid sequence according to the invention into a cloning vector can easily be achieved when both the genes and the desired cloning vehicle have been cut with the same restriction enzyme(s) as complementary DNA termini are thereby produced.

Alternatively, it may be necessary to modify the restriction sites that are produced into blunt ends either by digesting the single-stranded DNA or by filling in the single-stranded termini with an appropriate DNA polymerase. Subsequently, blunt end ligation with an enzyme such as T4 DNA ligase may be carried out.

If desired, any restriction site may be produced by ligating linkers onto the DNA termini. Such linkers may comprise specific oligonucleotide sequences that encode restriction site sequences. The restriction enzyme cleaved vector and nucleic acid sequence may also be modified by homopolymeric tailing.

"Transformation", as used herein, refers to the introduction of a heterologous nucleic acid sequence into a host cell, irrespective of the method used, for example direct uptake or transduction. The heterologous nucleic acid sequence may be maintained through autonomous replication or alternatively, may be integrated into the host genome. If desired, the recombinant DNA molecules are provided with appropriate control sequences compatible with the designated host which can regulate the expression of the inserted nucleic acid sequence.

The recombinant nucleic acid molecule according to the invention preferably contains one or more marker activities that may be used to select for desired transformants, such as ampicillin and tetracycline resistance in pBR322, ampicillin resistance and β-galactosidase activity in pUC8.

A suitable host cell is a cell which can be transformed by a nucleic acid sequence encoding a polypeptide or by a recombinant nucleic acid molecule comprising such a nucleic acid sequence and which can if desired be used to express said polypeptide encoded by said nucleic acid sequence. The host cell can be of procaryotic origin, e.g. bacteria such as *Escherichia coli, Bacillus subtilis* and *Pseudomonas species*; or of eucaryotic origin such as yeasts, e.g. *Saccharomyces cerevisiae* or higher eucaryotic cells such as insect, plant or mammalian cells, including HeLa cells and Chinese hamster ovary (CHO) cells. Insect cells include the Sf9 cell line of Spodoptera frugiperda (Luckow et al., Bio-technology 6, 47–55, 1988). Information with respect to the cloning and expression of the nucleic acid sequence of the present invention in eucaryotic cloning systems can be found in Esser, K. et al. (Plasmids of Eukaryotes, Springer-Verlag, 1986).

In general, prokaryotes are preferred for cloning of DNA sequences in constructing the vectors useful in the invention. For example E.coli K12 is particularly useful. Other microbial strains which may be used include E. coli strains such as DH5α or JM101.

For expression nucleic acid sequences of the present invention are operably linked to expression control sequences. Such control sequences may comprise promoters, enhancers, operators, inducers, ribosome binding sites etc.

When the host cells are bacteria, illustrative useful expression control sequences include the Trp promoter and operator (Goeddel, et al., Nucl. Acids Res. 8, 4057, 1980); the lac promoter and operator (Chang, et al., Nature 275, 615, 1978); the outer membrane protein promoter (Nakamura, K. and Inouge, M., EMBO J. 1, 771–775, 1982); the bacteriophage λ promoters and operators (Remaut, E. et al., Nucl. Acids Res. 11, 4677–4688, 1983); the α-amylase (B. subtilis) promoter and operator, termination sequence and other expression enhancement and control sequences compatible with the selected host cell. When the host cell is yeast, illustrative useful expression control sequences include, e.g., α-mating factor. For insect cells the polyhedrin or p10 promoters of baculoviruses can be used (Smith, G. E. et al., Mol. Cell. Biol. 3, 2156–65, 1983). When the host cell is of mammalian origin illustrative useful expression control sequences include, e.g., the SV-40 promoter (Berman, P. W. et al., Science 222, 524–527, 1983) or, e.g. the metallothionein promoter (Brinster, R. L., Nature 296, 39–42, 1982) or a heat shock promoter (Voellmy et al., Proc. Natl. Acad. Sci. USA 82, 4949–53, 1985). Alternatively, also expression control sequences present in CAV, in particular those regulating the expression of ORF 1–3 may be applied. For maximizing gene expression, see also Roberts and Lauer (Methods in Enzymology 68, 473, 1979).

The present invention also comprises a polypeptide displaying immunological characteristics of a CAV related antigen, i.e. the polypeptide comprises one or more immunoreactive and/or antigenic determinants of a CAV related antigen, essentially free from the whole virus or other proteins with which it is ordinarily associated.

More particularly, the invention provides polypeptides comprising at least part of ORF-1, ORF-2 or ORF-3 having an amino acid sequence shown in SEQ ID NO:2, SEQ ID NO:3 and SEQ ID NO: 4, respectively.

It will be understood that derivatives of said amino acid sequences displaying the same immunological properties in essence, i.e. immunological equivalents, are also within the scope of the present invention.

In addition a polypeptide comprising a fragment of the ORF 1–3 polypeptides or functional equivalent thereof, which can be used for immunization of poultry against CAV infection or diagnostic purposes is included in the present invention. Various methods are known for detecting such usable polypeptide fragments within a known amino acid sequence.

Suitable immunochemically active polypeptide fragments of a polypeptide according to the invention containing (an) epitope(s) can be found by means of the method described in Patent Application WO 86/06487, Geysen, H.M. et al. (Prod. Natl. Acad. Sci. 81, 3998–4002, 1984), Geysen, H.M. et al. (J. Immunol. Meth. 102, 259–274, 1987) based on the so-called pep-scan method, wherein a series of partially overlapping polypeptides corresponding with partial sequences of the complete polypeptide under consideration, are synthesized and their reactivity with antibodies is investigated.

In addition, a number of regions of the polypeptide, with the stated amino acid sequence, can be designated epitopes on the basis of theoretical considerations and structural agreement with epitopes which are now known. The determination of these regions is based on a combination of the hydrophilicity criteria according to Hopp and Woods (Proc. Natl. Acad. Sci. 78, 3824–3828, 1981) and the secondary structure aspects according to Chou and Fasman (Advances in Enzymology 47, 45–148, 1987).

T-cell epitopes which may be necessary can likewise be derived on theoretical grounds with the aid of Berzofsky's amphiphilicity criterion (Science 235, 1059–62, 1987).

In another embodiment of the invention a polypeptide having an amino acid sequence encoded by a nucleic acid sequence mentioned above is used.

Immunization of poultry against CAV infection can, for example be achieved by administering to the animals a polypeptide according to the invention in an immunologically relevant context as a so-called subunit vaccine. The subunit vaccine according to the invention may comprise a polypeptide in a pure form, optionally in the presence of a pharmaceutically acceptable carrier. The polypeptide can optionally be covalently bonded to a non-related protein, which, for example can be of advantage in the purification of the fusion product. Examples are β-galactosidase, protein A, prochymosine, blood clotting factor Xa, etc.

In some cases the ability to raise neutralizing antibodies against these polypeptides per se may be low. Small fragments are preferably conjugated to carrier molecules in order to raise their immunogenicity. Suitable carriers for this purpose are macromolecules, such as natural polymers (proteins like key hole limpet hemocyanin, albumin, toxins), synthetic polymers like polyamino acids (polylysine, polyalanine), or micelles of amphiphilic compounds like saponins. Alternatively these fragments may be provided as polymers thereof, preferably linear polymers.

Polypeptides to be used in such subunit vaccines can be prepared by methods known in the art, e.g. by isolating said polypeptides from CAV, by recombinant DNA techniques or by chemical synthesis.

If required the polypeptides according to the invention to be used in a vaccine can be modified in vitro or in vivo, for example by glycosylation, amidation, carboxylation or phosphorylation.

An alternative to subunit vaccines are live vector vaccines. A nucleic acid sequence according to the invention is introduced by recombinant DNA techniques into a micro-organism (e.g. a bacterium or virus) in such a way that the recombinant micro-organism is still able to replicate thereby expressing a polypeptide coded by the inserted nucleic acid sequence.

For example the technique of in vivo homologous recombination can be used to introduce a heterologous nucleic acid sequence, e.g. a nucleic acid sequence according to the invention into the genome of the vector micro-organism.

First, a DNA fragment corresponding with an insertion region of the vector genome, i.e. a region which can be used for the incorporation of a heterologous sequence without disrupting essential functions of the vector such as those necessary for infection or replication, is inserted into a cloning vector according to standard recDNA techniques. Insertion-regions have been reported for a large number of micro-organisms (e.g. EP 80,806, EP 110,385, EP 83,286, EP 314,569, WO 88/02022 and WO 88/07088).

Second, if desired, a deletion can be introduced into the insertion region present in the recombinant DNA molecule obtained from the first step. This can be achieved for example by appropriate exonuclease III digestion or restriction enzyme treatment of the recombinant DNA molecule from the first step.

Third, the heterologous nucleic acid sequence is inserted into the insertion region present in the recombinant DNA molecule of the first step or in place of the DNA deleted from said recombinant DNA molecule. The insertion region DNA sequence should be of appropriate length as to allow homologous recombination with the vector genome to occur. Thereafter, suitable cells can be transformed with vector genomic DNA in the presence of the recombinant DNA molecule containing the insertion flanked by appropriate vector DNA sequences whereby recombination occurs between the corresponding regions in the recombinant DNA molecule and the vector genome. Recombinant vector progeny can now be produced in cell culture and can be selected for example genotypically or phenotypically, e.g. by hybridization, detecting enzyme activity encoded by a gene cointegrated along with the heterologous nucleic acid sequence, or detecting the antigenic heterologous polypeptide expressed by the recombinant vector immunologically.

Next, this recombinant micro-organism can be administered to the chickens for immunization whereafter it maintains itself for some time, or even replicates in the body of the inoculated animal, expressing in vivo a polypeptide coded for by the inserted nucleic acid sequence according to the invention resulting in the stimulation of the immune system of the inoculated animal. Suitable vectors for the incorporation of a nucleic acid sequence according to the invention can be derived from viruses such as (avian) pox viruses, e.g. vaccinia virus or fowl pox virus (EP 314,569 and WO 88/02022), herpes viruses such as HVT (WO 88/07088), adeno virus or influenza virus, or bacteria such as E. coli or specific Salmonella species. With recombinant microorganisms of this type, the polypeptide synthesized in the host cell can be exposed as a surface antigen. In this context fusion of the said polypeptide with OMP proteins, or pilus proteins of for example E. coli or synthetic provision of signal and anchor sequences which are recognized by the organism are conceivable. It is also possible that the said immunogenic polypeptide, if desired as part of a larger whole, is released inside the animal to be immunized. In all of these cases it is also possible that one or more immunogenic products will find expression which generate protection against various pathogens and/or against various antigens of a given pathogen.

A vaccine according to the invention can be prepared by culturing a host cell infected with a vector virus comprising a nucleic acid sequence according to the invention, whereafter virus containing cells and/or vector viruses grown in the cells can be collected, optionally in a pure form, and formed to a vaccine optionally in a lyophilized form.

Above-mentioned host cells comprising a nucleic acid sequence according to the invention can also be cultured under conditions which are favourable for the expression of a polypeptide coded by said nucleic acid sequence. Vaccines may be prepared using samples of the crude culture, host cell lysates or host cell extracts, although in another embodiment more purified polypeptides according to the invention are formed to a vaccine, depending on its intended use. In order to purify the polypeptides produced, host cells containing a nucleic acid sequence according to the invention are cultured in an adequate volume and the polypeptides produced are isolated from such cells or from the medium if the protein is excreted. Polypeptides excreted into the medium can be isolated and purified by standard techniques, e.g. salt fractionation, centrifugation, ultrafiltration, chromatography, gel filtration or immuno affinity chromatography, whereas intracellular polypeptides can be isolated by first collecting said cells, disrupting the cells, for example by sonication or by other mechanically disruptive means such as French press followed by separation of the polypeptides from the other intracellular components and forming the polypeptides to a vaccine. Cell disruption could also be accomplished by chemical (e.g. EDTA treatment) or enzymatic means such as lysozyme digestion.

As mentioned earlier, the classical way of attenuating a virus has some disadvantages. Routinely this is done by inducing specific mutations by treatment with chemicals or by giving serial passages in a heterologous host animal or in tissue culture. The random way these mutations occur in the viral genome is the critical aspect of these techniques, as they are difficult to locate or to repeat in case spontaneous revertants occur. With the development of the recombinant DNA technology the possibility exists to manipulate the viral genome in a very precise way. As reviewed by Murphy et al., (Immunization against viruses, in: Fields, B. N. et al. eds., Virology $2^{nd}$ ed., Raven Press, N.Y. 1990) several possibilities exist for attenuating a virus by mutation of its genome, for instance by deletions, insertions or substitutions in a non-essential gene or part of it, or by insertions, substitutions, or deletions in regulatory regions, etc.

An example of the way in which such an attenuated CAV mutant not occurring in nature could be developed, using recDNA technology is described below.

First, the CAV genomic regions where the mutations can be situated are determined. These can be both the coding or the non-coding regions, for instance in the regulatory region, or the region coding for (part of) the viral adhesion-protein, or the factors determining host specificity.

Next, the mutations, e.g. deletions and/or insertions and/or substitutions can be introduced into the viral genome according to methods described before for the establishment of a recombinant vector.

Thus, an attenuated CAV not occurring in nature having a mutation in its genome introduced by recombinant DNA techniques also is within the scope of the present invention.

Antibodies or antiserum directed against a polypeptide according to the invention have potential use in passive immunotherapy, diagnostic immunoassay's and generation of anti-idiotype antibodies.

The CAV related polypeptides ORF 1–3 as described above can be used to produce antibodies, both polyclonal, monospecific and monoclonal. If polyclonal antibodies are desired, techniques for producing and processing polyclonal sera are known in the art (e.g. Mayer and Walter, eds, Immunochemical Methods in Cell and Molecular Biology, Academic Press, London, 1987). In short, a selected mammal, e.g. rabbit is given (multiple) injections with one of the above-mentioned immunogens, about 20 µg to about 80 µg of protein per immunization. Immunization are given with an acceptable adjuvant, generally equal volumes of immunogen and adjuvant. Acceptable adjuvants include Freund's complete, Freund's incomplete, alum-precipitate or water-in-oil emulsions, with Freund's complete adjuvant being preferred for the initial immunization. Freund's incomplete adjuvant is preferred for all booster immunizations. The initial immunization consists of the administration of about 1 ml of emulsion at multiple subcutaneous sites on the backs of the rabbits. Booster immunizations utilizing an equal volume of immunogen are given at about one month intervals and are continued until adequate levels of antibodies are present in an individual rabbits serum. Blood is collected and serum isolated by methods known in the art.

Monospecific antibodies to each of the immunogens are affinity purified from polyspecific antisera by a modification of the method of Hall et al. (Nature 311, 379–387 1984), prepared by immunizing rabbits as described above with the purified proteins. Monospecific antibody as used herein is defined as a single antibody species or multiple antibody species with homogeneous binding characteristics for the relevant antigen. Homogeneous binding as used herein refers to the ability of the antibody species to bind to a specific antigen or epitope.

Monoclonal antibody reactive against each of the CAV immunogens can be prepared by immunizing inbred mice, preferably Balb/c with the appropriate protein. The mice are immunized intraperitoneally with about 100 ng to about 10 µg immunogen per 0.5 ml doses in an equal volume of an acceptable adjuvant. Such acceptable adjuvants include Freund's complete, Freund's incomplete, alum-precipitate and water-in-oil emulsions. The mice are given intravenous booster immunizations of an equal amount of the immunogen without adjuvant at about days 14, 21 and 63 post primary immunization. At about day three after the final booster immunization individual mice are serologically tested for anti-immunogen antibodies. Spleen cells from antibody producing mice are isolated and fused with murine myeloma cells, such as SP-2/0 or the like, by techniques known in the art (Kohler and Milstein, Nature 256; 495–497, 1975). Hybridoma cells are selected by growth in hypoxanthine, thymidine and aminopterin in an appropriate cell culture medium such as Dulbecco's modified Eagle's medium (DMEM). Antibody producing hybridomas are cloned, preferably using the soft agar technique of MacPherson, (Soft Agar Techniques, Tissue Culture Methods and Applications, Kruse and Paterson, eds. Academic Press, 276, 1973), Discrete colonies are transferred into individual wells of culture plates for cultivation in an appropriate culture medium. Antibody producing cells are identified by screening with the appropriate immunogen. Immunogen positive hybridoma cells are maintained by techniques known in the art. Specific anti-monoclonal antibodies are produced by cultivating the hybridomas in vitro or preparing ascites fluid in mice following hybridoma injection by procedures known in the art.

Anti-idiotype antibodies are immunoglobulins which carry an "internal image" of the antigen of the pathogen against which protection is desired and can be used as an immunogen in a vaccine (Dreesman et al., J. Infect. Disease 151, 761, 1985). Techniques for raising anti-idiotype antibodies are known in the art (MacNamara et al., Science 226, 1325, 1984).

The vaccine according to the invention can be administered in a conventional active immunization scheme: single or repeated administration in a manner compatible with the dosage formulation and in such amount as will be prophylactically and/or therapeutically effective and immunogenic. The administration of the vaccine can be done, e.g. intradermally, subcutaneously, intramuscularly, intraperitonially, intravenously or intranasally.

Additionally the vaccine may also contain an aqueous medium or a water containing suspension, often mixed with other constituents, e.g. in order to increase the activity and/or shelf life. These constituents may be salts, pH buffers, stabilizers (such as skimmed milk or casein hydrolysate), emulsifiers adjuvants to improve the immune response (e.g. oils, muramyl dipeptide, aluminium-hydroxide, saponin, polyanions and amphipathic substances) and preservatives.

It is clear that a vaccine according to the invention may also contain immunogens related to other pathogens of poultry or may contain nucleic acid sequences encoding these immunogens, like antigens of Infectious Bronchitis Virus, Newcastle Disease virus Infectious Bursal Disease virus or Marek's Disease Virus to produce a multivalent vaccine.

The invention also relates to an "immunochemical reagent", which reagent comprises at least one of the polypeptides according to the invention or an antigenic fragment thereof.

The term "immunochemical reagent" signifies that the polypeptides according to the invention have been bound to a suitable support or have been provided with a labelling substance.

The supports which can be used are, for example, the inner wall of a microtest well or a cuvette, a tube or capillary, a membrane, filter, test strip or the surface of a particle such as, for example, a latex particle, an erythrocyte, a dye sol, a metal sol or metal compound as sol particle.

Labelling substances which can be used are, inter alia, a radioactive isotope, a fluorescent compound, an enzyme, a dye sol, metal sol or metal compound as sol particle.

A nucleic acid sequence according to the invention can also be used to design specific probes for hybridization experiments for the detection of CAV related nucleic acids in any kind of tissue.

The present invention also provides a test kit comprising said nucleic acid sequence useful for the diagnosis of CAV infection.

The invention also relates to a test kit to be used in an immuno-assay, this test kit containing at least one immunochemical reagent according to the invention.

The immunochemical reaction which takes place using this test kit is preferably a sandwich reaction, an agglutination reaction, a competition reaction or an inhibition reaction.

For carrying out a sandwich reaction, the test kit can consist, for example, of a polypeptide according to the invention bonded to a solid support, for example the inner wall of a microtest well, and either a labelled polypeptide according to the invention or a labelled anti-antibody.

EXAMPLE 1

Origin of CAV strain 26P4

At Intervet America (Millsboro, Del.) 8 weeks old sentinal SPF chicken (which were seronegative for CAV) were kept in the presence of birds showing signs of seroconversion towards CAV infection. After two weeks a 20% v/v homogenate in RPMI of the liver of these sentinel birds was made and filtered through 0.2 µm filter. This filtrate was incubated in tissue culture flasks with MDCC-MSB1 cells (Akiyama et al., Biken J. 17, 105–117, 1974), which are suited host cells for CAV (Goryo et al., Avian pathology 16, 149–163, 1987). One of the isolates, marked 26P4, was identified as CAV, based on CPE and positive immunofluorescence with the positive anti-CAV-serum provided by the USDA.

Culturing of 26P4

Culturing of 26P4 virus was performed on MDCC-MSB1 cells in tissue culture flasks, according to the state of the art (Goryo et al., ibid).

Cloning of the viral genome

To isolate the replicative form (RF) of the viral DNA of CAV strain 26P4, 500 ml culture of MSB1 cells was prepared containing $10^6$ cells/ml and infected with a virus titre of approximately $10^6$ $TCID_{50}$/ml. Viral DNA was prepared using a standard Hirt extraction (McMaster et al., J. Virol 38, 317–326, 1981). The time point after infection at which to obtain maximal amount of the RF viral DNA, was established in a timecourse experiment to be 30 hours post infection.

The DNA from infected cells was analyzed on a 0.8% agarose/Ethidiumbromide gel, and the 1.7 kb band representing the circular viral RF DNA was isolated from agarose gel using NA45 DEAE membranes (Schleicher and Schull) according to standard protocols (Maniatis et al., 1989, ibid).

500 ng of viral DNA was digested with 20 U of either Hind III or Bam HI restriction endonuclease, in a 25 µl volume. 2 µg bacterial plasmid pGEM 7zf+ (Promega corp.) was also digested with either Hind III or Bam HI, dephosphorylated, and incubated with proteinase K (Maniatis et al., 1989, ibid). Vector and insert DNA preparations were extracted with phenol/chloroform and precipitated with 2 volumes of 96% Ethanol and 1/10 volume of 3 M Sodium Acetate pH 6.0. Ligation of vector and insert DNA with T4 DNA ligase was performed according to standard procedures (Maniatis et al., 1989, ibid). The ligation mixture was used to transform *E.coli* DH5α competent cells (Clontech corp.) which were then plated onto LB-agar plates containing 100 µg/ml ampicillin (Ap). Plasmid DNA was isolated from Ap resistant colonies and screened for 2.3 kb inserts by restriction enzyme analysis.

Figure 1A:
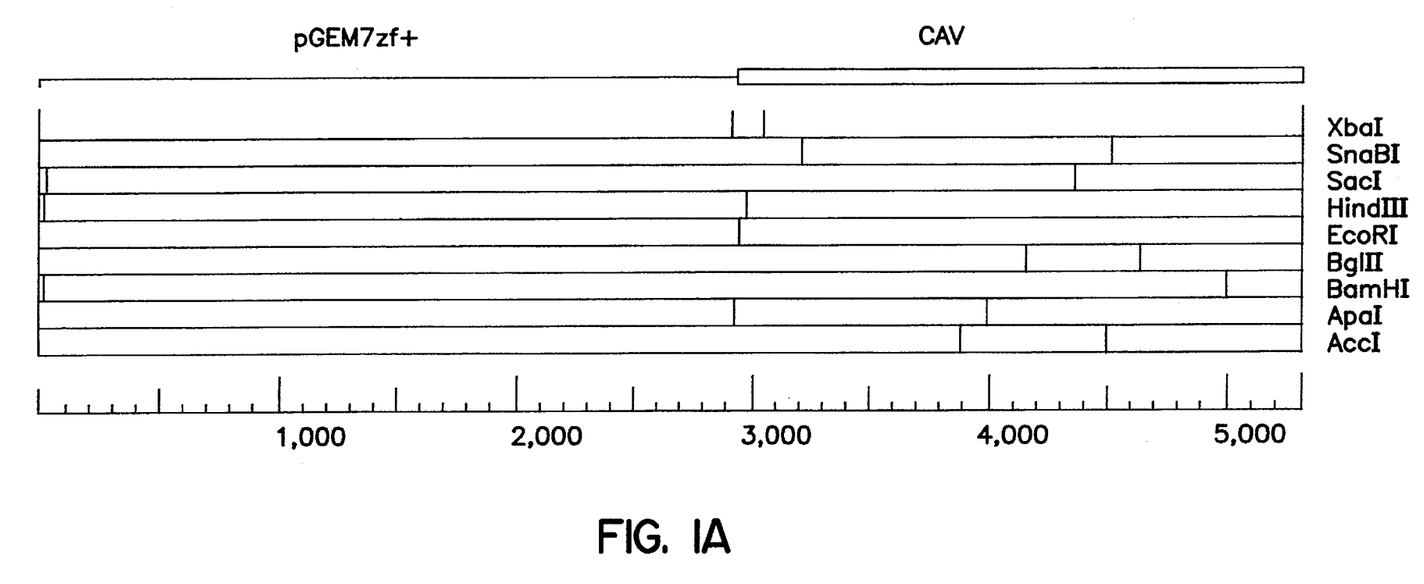
Figure 1B:
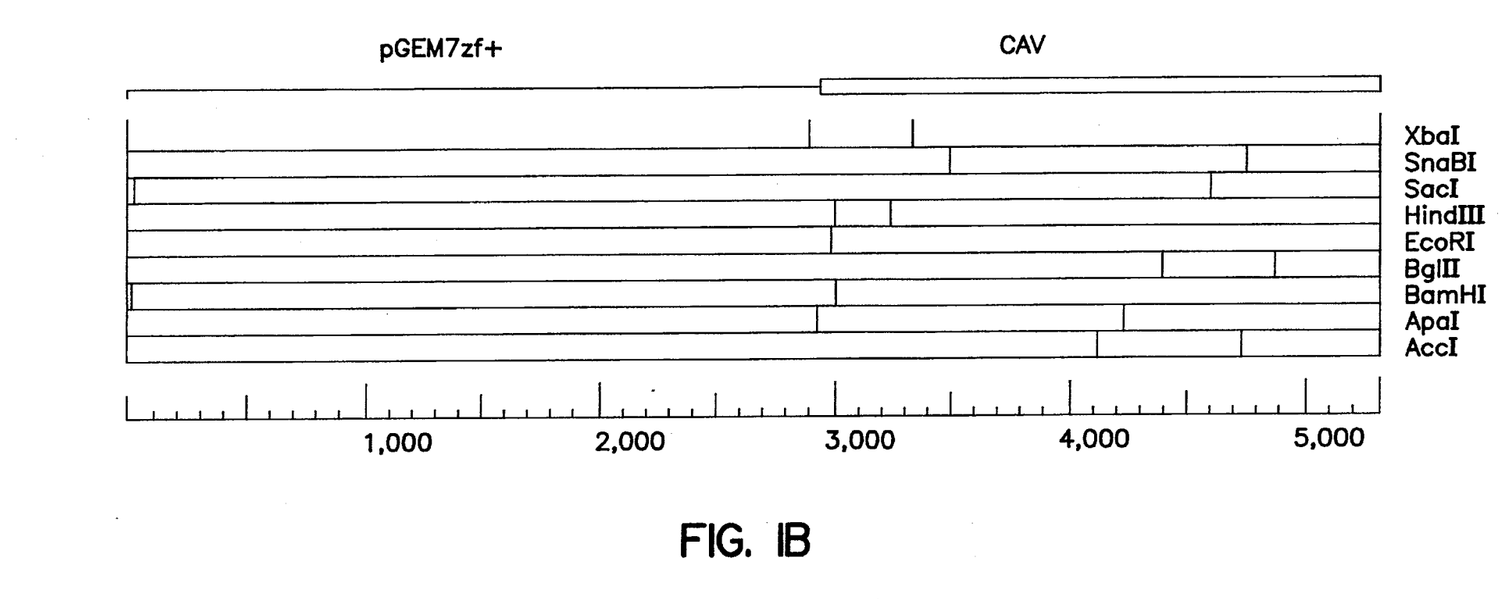

Two plasmids were identified: pCA1, containing the Hind III digested 2.3 kb CAV RF DNA, and pCA3, which has the Bam HI digested CAV RF DNA inserted in opposite direction, compared to pCA1. Both plasmid are described in FIG. 1, by giving their restriction pattern.

EXAMPLE 2

DNA sequence analysis

To determine the DNA sequence of the CAV genome, progessively deleted fragments were generated according to Henikoff (Gene 28, 351, 1984): 5 µg of pCA1 and of pCA3 was incubated with Sph I and next with Cla I restriction enzyme. After proteinase K incubation, phenol/chloroform treatment, and ethanol precipitation, samples were incubated with Exonuclease III for increasing time-intervals. DNA fragments were made blunt end with S1 nuclease and Klenow polymerase, and finally circularized with T4 DNA ligase, transformed into *E. coli* DH5α competent cells and plated onto ampicillin plates. Plasmid DNA from resistant colonies was analyzed for the size of the insert.

DNA sequence analysis was performed as published by Sanger et al. (Proc. Natl. Acad. Sci. USA 74, 5463, 1977), using the dideoxy-chain termination technique directly on the double stranded plasmid DNA of mini preparations. The T7 and Sp6 promoter primers were used, hybridizing directly up- and downstream of the pGEM 7zf+ multiple cloning site.

Sequence data was collected, assembled, and analysed on an IBM PC using the Gene Master program (BioRad corp.).

EXAMPLE 3

Insertion of the CAV DNA comprising ORF 1 into the viral genome of Herpes Virus of Turkeys (HVT)

CAV RF DNA was isolated as outlined in example 1. To prepare the ORF 1 for insertion and efficient expression in HVT, particularly the sequences preceding the first ATG codon had to be trimmed down to a minimum of leader sequence. Therefor, 2 µg of the CAV RF DNA was digested with restriction enzymes Apa I and Mro I. These digestions give a linear molecule of CAV RF DNA, with the ORF 1 situated in the middle, and the first ATG of ORF 1 at the side of the Mro I site. After inactivation, phenol extraction and ethanol precipitation, these fragments were incubated for increasing time intervals with exonuclease III, and made blunt end, as described in example 2. As exonuclease cannot digest 3' overhanging sites like from Apa I, the RF DNA fragment is digested from the Mro I site in the direction of the first ATG of ORF 1. The blunted fragments were ligated by T4 ligase with a 50 fold molar excess of EcoR V linkers (B. Mannheim corp.) that had been phosphorylated, all according to standard procedures. The linker-ligation mixture was digested with EcoR V, and inactivated at 65° C. for 10 minutes. This mixture was ligated with 500 ng of EcoR V digested and dephosphorylized pGEM5zf+vector (Promega corp.). The ligation mixture was transformed into *E.coli* DH5α competent cells and plated onto Ap plates. Miniprep DNA isolations of resistant colonies was analyzed for the remaining size of the plasmid insert by double digestion with Apa I and Spe I. Inserts with a size of approximately 1.9 kb were studied for their orientation by restriction analysis, and examined by Sanger sequencing, with either Sp6 or T7 primers.

This way plasmid pCA4 was established, having a 1.9 kb CAV insert composed of the sequence from nucleotides 860 to 2298 continued in 1 to 475 as depicted in SEQ ID NO: 1; ligated to EcoR V linkers, and inserted into EcoR V digested pGEM5zf+. Especially the short leader sequence, preceding the first ATG of the insert was validated by Sanger sequencing not to contain any additional ATG codon.

Figure 3:
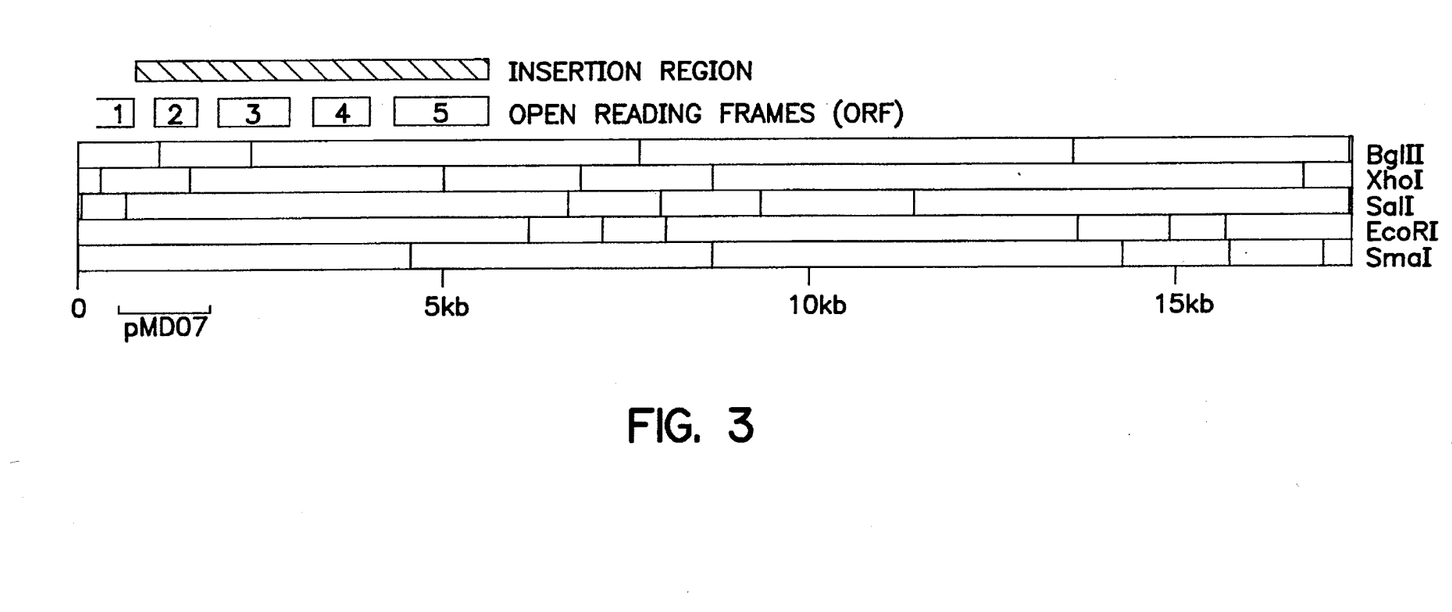

Based on the genome structure of HVT as published by Igarashi, T. et al. (Virology 157, 351, 1987) a region in the unique-short sequence element (Us) of the virus was selected for the insertion of foreign genes. The corresponding DNA fragment was screened from a λEMBL3 library constructed by partially digesting total DNA from HVT infected CEF. The insert of one of the λ-isolates, characterized by the absence of any BamHI restriction site, was denominated λHVT04 and analyzed in detail by physical mapping (FIG. 3). The sequence present in the 17.5 kb inserted fragment represented a major part of the Us region including part of the inverted repeat structure (Igarashi, T. et al., 1987, ibid). One of the 1.2 kb XhoI restriction fragments from λHVT04 was subcloned in pGEM3Z digested with Sal I resulting in plasmid pMDO7 which contained a unique BglII site available for insertion of DNA fragments.

Figure 4:
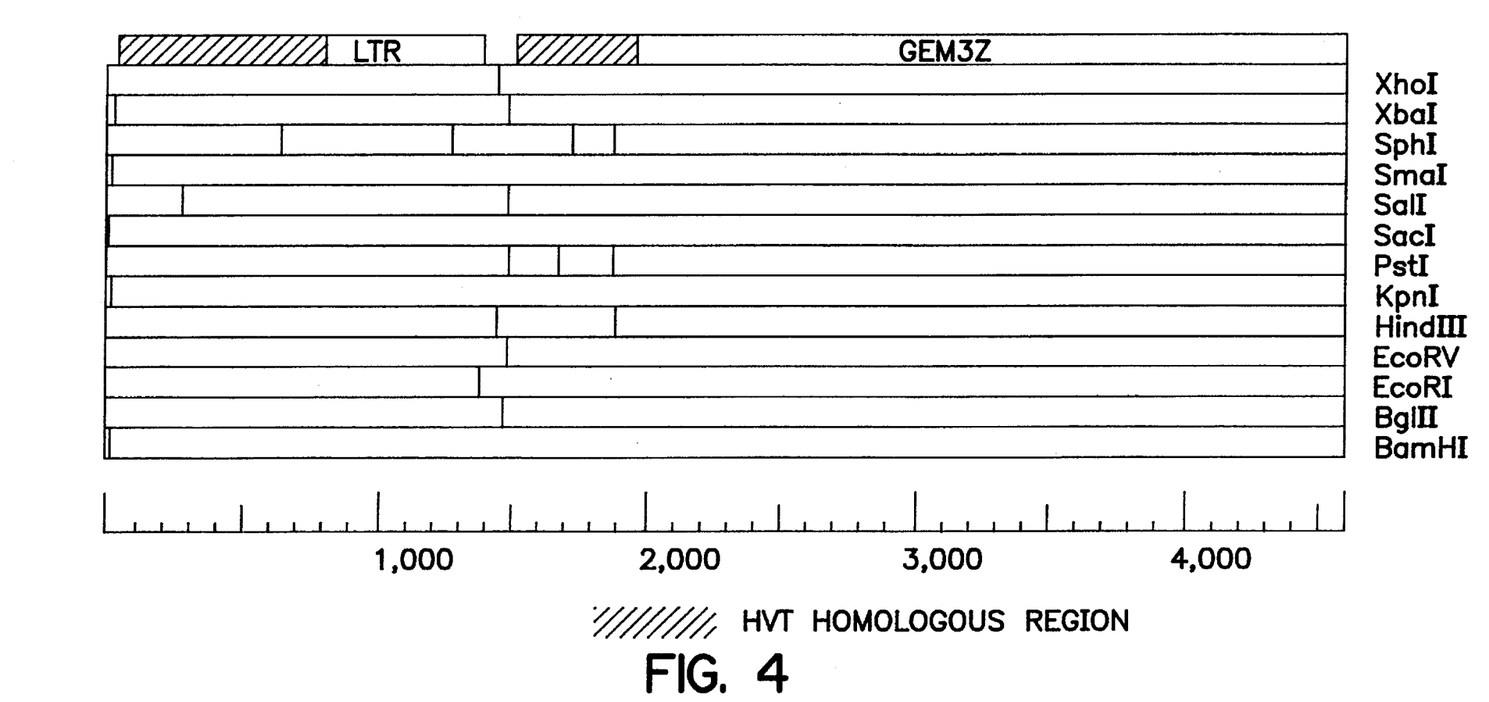

A strong promoter which could direct the expression of foreign genes after their insertion into the genome of the HVT virus was selected from the LTR sequence of Rous Sarcoma Virus (RSV). The promoter has been mapped on a 580 bp NdeI/HindIII restriction fragment from pRSVcat (Gorman et al., Proc. Natl. Acad. Sci. 79, 6777, 1982) and was inserted between the HindIII and PstI sites of pGEM3Z (Promega) by means of double stranded synthetic linkers on both sites of the fragment. The connection between the HindIII site from the vector pGEM3Z and the NdeI site of the RSV fragment carrying the LTR-promoter was made with a 30 bp linker containing cohesive ends compatible with HindIII on one and NdeI on the other site. However, after ligation both restriction sites are not restored due to deliberate modifications in the outer nucleotides of the six basepair recognition sequence. In addition to the removal of these two sites, a new restriction site (BamHI) present within the linker itself was created at the corresponding position. A second 20 bp linker was synthesized which connected the HindIII site from the LTR fragment to the PstI site from pGEM3Z, in this case without destruction of the recognition sequence on either of the ends and adding the three convenient unique restriction sites BglII, XhoI and EcoR V, to those already present in the polylinker of pGEM3Z, e.g. PstI, SalI, XhoI and BamHI. The resulting derivative of pGEM3Z, designated pVECO1, therefore contains a 650 bp restriction fragment carrying the LTR promoter sequence immediately followed by seven restriction sites available for the insertion of foreign genes. The 650 bp fragment is flanked on either end by a BamHI restriction site and has been transferred as such to the unique BglII site present in the 1, 2 kb HVT insert from pMDO7. The cohesive ends generated by these two restriction enzymes are compatible but ligation does not restore either of the original recognition sequences for BglII or BamHI. One of the resulting constructs, carrying the LTR in the orientation towards the TR$_s$, was designated pVECO4 and checked by restriction mapping (FIG. 4). The structure of this universal HVT recombination vector allows the insertion of foreign genes immediately downstream of the LTR promoter and subsequent integration of the complete expression cassette into the HVT genome by in vivo recombination. The positions of the different restriction sites downstream of the LTR in particular those for the enzymes BglII, XhoI and Ecor V are designed in such a way that even multiple gene insertion can be envisaged.

The CAV DNA insert from pCA4 was removed from the plasmid by EcoR V digestion and inserted into EcoR V digested and dephosphorylated pVECO4. Once again the orientation of the inserted fragment was checked, and the plasmid having the right orientation was denominated pCA5.

Linearized DNA from plasmid pCA5 was introduced together with total DNA prepared from HVT infected cells into CEF by a method based on the calcium phosphate DNA precipitation according to Graham, F. and v.d. Eb, A., (Virology .52, 456, 1973). Two micrograms of plasmid DNA from the construct was mixed with 15 µg of DNA from HVT linearized infected cells in a final volume of 560 µl $H_2O$ and added to 750 µl of HBSP (20 mM KCl, 560 mM NaCl, 24 mM glucose, 3 mM $Na_2HPO_4$, 100 mM HEPES, pH 7.0). Precipitate was formed by gradually adding 190 µl of 1M $CaCl_2$ solution and incubating the mixtures at room temperature for 30 minutes. In the meantime, 15 ml of a suspension of secondary CEF from 10 day old embryos in medium 6/B8, for which the composition is based on Glasgow's modification of Eagle's Minimal Essential Medium supplemented with 2% of fetal calf serum, were seeded in ø 10 cm dishes at a density of $5\times10^5$ cells per ml. Calcium phosphate precipitated DNA was gently added to the cell suspension and dishes were incubated at 37° C. in a humified incubator containing 5% $CO_2$ in air. After 5 hours, medium was removed and 10 ml of solution containing equal volumes of HBSP and 30% glycerol was layered onto the cells. After a one to two minute incubation, the solution was removed, cells were washed with medium 6/B8 and dishes were incubated with fresh medium for 3 to 5 days until viral CPE developed. Detection of HVT recombinants expressing the CAV related polypeptide was done by immunofluorescence staining using specific mono- or polyvalent sera against these CAV antigens.

BRIEF DESCRIPTION OF THE DRAWINGS

FIGS. 1A and 1B:

Representation of the endonuclease restriction enzyme pattern of the plasmids pCA1 and pCA3.

A. Plasmid pCA1 is depicted as a molecule linearized by Hind III digestion.

B. Plasmid pCA3 is depicted as a molecule linearized by Bam HI digestion.

FIG. 2:

The shaded areas represent the open reading frames (ORF) that are present in the DNA sequence of RF DNA of CAV strain 26P4. The ORFs are numbered ORF1, ORF2 and ORF3, from top to bottom. The CAV RF DNA is represented as a molecule linearized by Dra I digestion.

FIG. 3:

Restriction enzyme map of a DNA fragment essentially corresponding to the Us region of the HVT genome. The relative position of the insertion-region consisting of four open reading frames and non-coding sequences in between is indicated.

FIG. 4:

Restriction enzyme map of pVECO4 showing the LTR-promoter inserted into the unique BglII site of the 1, 2 kb XhoI HVT fragment from pMDO7.

We claim:

1. An isolated and purified DNA molecule comprising a chicken anemia virus DNA fragment encoding a polypeptide having an amino acid sequence shown in SEQ ID NO:2, wherein said DNA fragment is substantially free of other chicken anemia virus DNA that codes for other chicken anemia virus polypeptides.

2. A DNA molecule according to claim 1, wherein the DNA molecule comprises the nucleic acid sequence of ORF-1 shown in SEQ ID NO:1.

3. A recombinant nucleic acid molecule comprising a DNA molecule according to claims 1 or 2.

4. A recombinant nucleic acid molecule according to claim 3, wherein the nucleic acid sequence is linked to an expression control sequence.

5. A viral vector comprising a DNA molecule according to claims 1 or 2.

6. A cultered host cell transformed with a DNA molecule according to claims 1 or 2.

7. A host cultered cell transformed with a recombinant nucleic acid molecule according to claim 3.

8. A host cultered cell transformed with a recombinant nucleic acid molecule according to claim 4.

9. A cultured host cell containing a viral vector according to claim 5.

* * * * *

UNITED STATES PATENT AND TRADEMARK OFFICE
CERTIFICATE OF CORRECTION

PATENT NO. : 5,554,525
DATED : September 10, 1996
INVENTOR(S) : SONDERMEIJER ET AL.

It is certified that error appears in the above-indentified patent and that said Letters Patent is hereby corrected as shown below:

Column 24,

Claim 6, line 1, delete "cultered" and replace with -- cultured --.

Claim 7, line 1, delete "host cultered" and replace with

-- cultured host --.

Claim 8, line 1, delete "host cultered" and replace with

-- cultured host --.

Signed and Sealed this

Seventh Day of January, 1997

Attest:

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2298 base pairs
        ( B ) TYPE: nucleic acid
        ( C ) STRANDEDNESS: single
        ( D ) TOPOLOGY: circular     ( i i ) MOLECULE TYPE: DNA (genomic)

( v i ) ORIGINAL SOURCE:
        ( A ) ORGANISM: Chicken Anemia Virus
        ( C ) INDIVIDUAL ISOLATE: 26P4

( i x ) FEATURE:
        ( A ) NAME/KEY: CDS
        ( B ) LOCATION: 876..2225
        ( D ) OTHER INFORMATION: /label=ORF1

( i x ) FEATURE:
        ( A ) NAME/KEY: CDS
        ( B ) LOCATION: 101..502
        ( D ) OTHER INFORMATION: /label=ORF2

( i x ) FEATURE:
        ( A ) NAME/KEY: CDS
        ( B ) LOCATION: 403..1053
        ( D ) OTHER INFORMATION: /label=ORF3

( x i ) SEQUENCE DESCRIPTION: SEQ ID NO:1:

```
AAATAGCACT CAATAAACGC AGCAAATGGC TTAATCGCAC AATCGCATTC CGAGTGGTTA      60
CTATTCCATC ACCATTCTAG CCTGTACACA GAAAGTCAAG ATGGACGAAT CGCGAGACTT     120
CGCTCGCGAT TCGTCGAAGG CGGGGGGCCG GAGGCCCCCC GGTGGCCCCC CTCCAACGAG     180
TGGAGCATGT ACAGGGGGGT ACGTCATCCG TACAGGGGGG TACGTCACAA AGAGGCGTTA     240
CCGTACAGGG GGGTACGTCA CGCGTACAGG GGGGTACGTC ACAGCCAATC AGAAGCTGCC     300
ACGTTGCGAA AGTGACGTTT CGAAAATGGG CGGCGCGAGC CTCTCTATAT ATTGCGCGCA     360
CATACCGGTC GGCAGTAGGT ATACGCAAGG CGGTCCGGGT GGATGCACGG AACGGCGGA      420
CAACCGGCCG CTGGGGGCAG TGAATCGGCG CTTAGCCGAG AGGGGCAACC TGGGCCCAGC     480
GGAGCCGCGC AGGGGCAAGT AATTTCAAAT GAACGCTCTC AAGAAGATA CTCCACCCGG      540
ACCATCAACG GTGTTCAGGC CACCAACAAG TTCACGGCCG TTGGAAACCC CTCACTGCAG     600
AGAGATCCGG ATTGGTATCG CTGGAATTAC AATCACTCTA TCGCTGTGTG GCTGCGCGAA     660
TGCTCGCGCT CCCACGCTAA GATCTGCAAC TGCGGACAGT TCAGAAAGCA CTGGTTTCAA     720
GAATGCGCCG GACTTGAGGA CCGATCAACC CAAGCCTCCC TCGAAGAAGC GATCCTGCGA     780
CCCCTCCGAG TACAGGGTAA GCGAGCTAAA AGAAAACTTG ATTACCACTA CTCCCAGCCG     840
ACCCCGAACC GCAAGAAGGT GTATAAGACT GTAAGATGGC AAGACGAGCT CGCAGACCGA     900
GAGGCCGATT TTACGCCTTC AGAAGAGGAC GGTGGCACCA CCTCAAGCGA CTTCGACGGA     960
GATATAAATT TCGACATCGG AGGAGACAGC GGTATCGTAG ACGAGCTTTT AGGAAGGCCT    1020
TTCACAACCC CCGCCCCGGT ACGTATAGTG TGAGGCTGCC GAACCCCCAA TCTACTATGA    1080
CTATCCGATT CCAAGGAGTC ATCTTTCTCA CGGAAGGACT CATTCTGCCT AAAAACAGCA    1140
CAGCGGGGGG CTATGCAGAC CACATGTACG GGCGAGAGT CGCCAAGATC TCTGTAAACC     1200
TGAAAGAGTT CCTGCTAGCG TCAATGAACC TGACATACGT GAGCAAAATC GGAGGACCCA    1260
TCGCCGGTGA GTTGATTGCG GACGGGTCTA AATCACAAGC CGCGGAGAAT TGGCCTAATT    1320
GCTGGCTGCC GCTAGATAAT AACATGCCCT CCGCGACACC ATCGGCATGG TGGAGATGGG    1380
CCTTAATGAT GATGCAGCCC ACGGACTCTT GCCGGTTCTT TAATCACCCT AAGCAGATGA    1440
CCCTGCAAGA CATGGGTCGC ATGTTTGGGG CTGGCACCT GTTCCGACAC ATTGAAACCC     1500
GCTTTCAGCT CCTTGCCACT AAGAATGAGG GATCCTTCAG CCCCGTGGCG AGTCTTCTCT    1560
CCCAGGGAGA GTACCTTACG CGTCGGGACG ATGTTAAGTA CAGCAGCGAT CACCAGAACC    1620
GGTGGCGAAA AGGCGGACAA CCGATGACGG GGGTATTGC TTATGCGACC GGGAAAATGA     1680
GACCCGACGA GCAACAGTAC CCTGCTATGC CCCCAGACCC CCCGATCATC ACCACTACTA    1740
CAGCCCAAGG CACGCAAGTC CGCTGCATGA ATAGCACGCA AGCTTGGTGG TCATGGGACA    1800
CATATATGAG CTTTGCAACA CTCACAGCAC TCGGTGCACA ATGGTCTTTT CCTCCAGGGC    1860
AACGTTCAGT TTCTAGACGG TCCTTCAACC ACCACAAGGC GAGAGGAGCC GGGGACCCCA    1920
AAGGCCAGAG ATGGCACACG CTGGTGCCCC TGGGCACGGA GACCATCACC GACAGCTACA    1980
TGAGTGCACC CGCATCAGAG CTGGACACTA ATTTCTTTAC GCTTTACGTA GCGCAAGGCA    2040
CAAATAAGTC GCAGCAGTAC AAGTTCGGCA CAGCTACATA CGCGCTAAAG GAGCCGGTAA    2100
TGAAAAGCGA TGCATGGGCA GTGGTACGCG TCCAGTCGGT CTGGCAGCTG GGTAACAGGC    2160
AGAGGCCATA CCCATGGGAC GTCAACTGGG CCAACAGCAC CATGTACTGG GAGACGCAGC    2220
CCTGAAAAGG GGGGGGGGCT AAAGCCCCCC CCCCTTGAAC CCCCCCCTGG GGGGGATTCC    2280
CCCCCAGCCC CCCCCTTT                                                  2298
```

( 2 ) INFORMATION FOR SEQ ID NO:2:

( i ) SEQUENCE CHARACTERISTICS:
        ( A ) LENGTH: 449 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

```
Met Ala Arg Arg Ala Arg Arg Pro Arg Gly Arg Phe Tyr Ala Phe Arg
 1               5                  10                  15
Arg Gly Arg Trp His His Leu Lys Arg Leu Arg Arg Arg Tyr Lys Phe
            20                  25                  30
Arg His Arg Arg Arg Gln Arg Tyr Arg Arg Arg Ala Phe Arg Lys Ala
        35                  40                  45
Phe His Asn Pro Arg Pro Gly Thr Tyr Ser Val Arg Leu Pro Asn Pro
    50                  55                  60
Gln Ser Thr Met Thr Ile Arg Phe Gln Gly Val Ile Phe Leu Thr Glu
65                  70                  75                  80
Gly Leu Ile Leu Pro Lys Asn Ser Thr Ala Gly Gly Tyr Ala Asp His
                85                  90                  95
Met Tyr Gly Ala Arg Val Ala Lys Ile Ser Val Asn Leu Lys Glu Phe
            100                 105                 110
Leu Leu Ala Ser Met Asn Leu Thr Tyr Val Ser Lys Ile Gly Gly Pro
        115                 120                 125
Ile Ala Gly Glu Leu Ile Ala Asp Gly Ser Lys Ser Gln Ala Ala Glu
    130                 135                 140
Asn Trp Pro Asn Cys Trp Leu Pro Leu Asp Asn Asn Met Pro Ser Ala
145                 150                 155                 160
Thr Pro Ser Ala Trp Trp Arg Trp Ala Leu Met Met Met Gln Pro Thr
                165                 170                 175
Asp Ser Cys Arg Phe Phe Asn His Pro Lys Gln Met Thr Leu Gln Asp
            180                 185                 190
Met Gly Arg Met Phe Gly Gly Trp His Leu Phe Arg His Ile Glu Thr
        195                 200                 205
Arg Phe Gln Leu Leu Ala Thr Lys Asn Glu Gly Ser Phe Ser Pro Val
    210                 215                 220
Ala Ser Leu Leu Ser Gln Gly Glu Tyr Leu Thr Arg Arg Asp Asp Val
225                 230                 235                 240
Lys Tyr Ser Ser Asp His Gln Asn Arg Trp Arg Lys Gly Gly Gln Pro
                245                 250                 255
Met Thr Gly Gly Ile Ala Tyr Ala Thr Gly Lys Met Arg Pro Asp Glu
            260                 265                 270
Gln Gln Tyr Pro Ala Met Pro Pro Asp Pro Pro Ile Ile Thr Thr Thr
        275                 280                 285
Thr Ala Gln Gly Thr Gln Val Arg Cys Met Asn Ser Thr Gln Ala Trp
    290                 295                 300
Trp Ser Trp Asp Thr Tyr Met Ser Phe Ala Thr Leu Thr Ala Leu Gly
305                 310                 315                 320
Ala Gln Trp Ser Phe Pro Pro Gly Gln Arg Ser Val Ser Arg Arg Ser
                325                 330                 335
Phe Asn His His Lys Ala Arg Gly Ala Gly Asp Pro Lys Gly Gln Arg
            340                 345                 350
Trp His Thr Leu Val Pro Leu Gly Thr Glu Thr Ile Thr Asp Ser Tyr
```

|     |     |     | 355 |     |     |     | 360 |     |     |     | 365 |     |     |
| --- | --- | --- | --- | --- | --- | --- | --- | --- | --- | --- | --- | --- | --- |

Met Ser Ala Pro Ala Ser Glu Leu Asp Thr Asn Phe Phe Thr Leu Tyr
     370                     375                 380

Val Ala Gln Gly Thr Asn Lys Ser Gln Gln Tyr Lys Phe Gly Thr Ala
385                      390                 395                      400

Thr Tyr Ala Leu Lys Glu Pro Val Met Lys Ser Asp Ala Trp Ala Val
             405                 410                     415

Val Arg Val Gln Ser Val Trp Gln Leu Gly Asn Arg Gln Arg Pro Tyr
             420                 425                     430

Pro Trp Asp Val Asn Trp Ala Asn Ser Thr Met Tyr Trp Glu Thr Gln
         435                 440                 445

Pro
449

( 2 ) INFORMATION FOR SEQ ID NO:3:

( i ) SEQUENCE CHARACTERISTICS:
        ( A ) LENGTH: 133 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:3:

Met Asp Glu Ser Arg Asp Phe Ala Arg Asp Ser Ser Lys Ala Gly Gly
 1               5                  10                   15

Arg Arg Pro Pro Gly Gly Pro Pro Pro Thr Ser Gly Ala Cys Thr Gly
             20                  25                  30

Gly Tyr Val Ile Arg Thr Gly Gly Tyr Val Thr Lys Arg Arg Tyr Arg
             35                  40                  45

Thr Gly Gly Tyr Val Thr Arg Thr Gly Gly Tyr Val Thr Ala Asn Gln
     50                  55                  60

Lys Leu Pro Arg Cys Glu Ser Asp Val Ser Lys Met Gly Gly Ala Ser
65                   70                  75                   80

Leu Ser Ile Tyr Cys Ala His Ile Pro Val Gly Ser Arg Tyr Thr Gln
             85                  90                  95

Gly Gly Pro Gly Gly Cys Thr Gly Thr Ala Asp Asn Arg Pro Leu Gly
             100                 105                 110

Ala Val Asn Arg Arg Leu Ala Glu Arg Gly Asn Leu Gly Pro Ala Glu
             115                 120                 125

Pro Arg Arg Gly Lys
     130

( 2 ) INFORMATION FOR SEQ ID NO:4:

( i ) SEQUENCE CHARACTERISTICS:
        ( A ) LENGTH: 216 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:4:

Met His Gly Asn Gly Gly Gln Pro Ala Ala Gly Gly Ser Glu Ser Ala
 1               5                  10                   15

Leu Ser Arg Glu Gly Gln Pro Gly Pro Ser Gly Ala Ala Gln Gly Gln
             20                  25                  30

Val Ile Ser Asn Glu Arg Ser Pro Arg Arg Tyr Ser Thr Arg Thr Ile
         35                  40                  45

-continued

| | | | | | | | | | | | | | | | |
|---|---|---|---|---|---|---|---|---|---|---|---|---|---|---|---|
| Asn | Gly | Val | Gln | Ala | Thr | Asn | Lys | Phe | Thr | Ala | Val | Gly | Asn | Pro | Ser |
| | 50 | | | | | 55 | | | | | 60 | | | | |
| Leu | Gln | Arg | Asp | Pro | Asp | Trp | Tyr | Arg | Trp | Asn | Tyr | Asn | His | Ser | Ile |
| 65 | | | | | 70 | | | | | 75 | | | | | 80 |
| Ala | Val | Trp | Leu | Arg | Glu | Cys | Ser | Arg | Ser | His | Ala | Lys | Ile | Cys | Asn |
| | | | | 85 | | | | | 90 | | | | | 95 | |
| Cys | Gly | Gln | Phe | Arg | Lys | His | Trp | Phe | Gln | Glu | Cys | Ala | Gly | Leu | Glu |
| | | | 100 | | | | | 105 | | | | | 110 | | |
| Asp | Arg | Ser | Thr | Gln | Ala | Ser | Leu | Glu | Glu | Ala | Ile | Leu | Arg | Pro | Leu |
| | | 115 | | | | | 120 | | | | | 125 | | | |
| Arg | Val | Gln | Gly | Lys | Arg | Ala | Lys | Arg | Lys | Leu | Asp | Tyr | His | Tyr | Ser |
| | 130 | | | | | 135 | | | | | 140 | | | | |
| Gln | Pro | Thr | Pro | Asn | Arg | Lys | Lys | Val | Tyr | Lys | Thr | Val | Arg | Trp | Gln |
| 145 | | | | | 150 | | | | | 155 | | | | | 160 |
| Asp | Glu | Leu | Ala | Asp | Arg | Glu | Ala | Asp | Phe | Thr | Pro | Ser | Glu | Glu | Asp |
| | | | | 165 | | | | | 170 | | | | | 175 | |
| Gly | Gly | Thr | Thr | Ser | Ser | Asp | Phe | Asp | Gly | Asp | Ile | Asn | Phe | Asp | Ile |
| | | | 180 | | | | | 185 | | | | | 190 | | |
| Gly | Gly | Asp | Ser | Gly | Ile | Val | Asp | Glu | Leu | Leu | Gly | Arg | Pro | Phe | Thr |
| | | 195 | | | | | 200 | | | | | 205 | | | |
| Thr | Pro | Ala | Pro | Val | Arg | Ile | Val | | | | | | | | |
| | 210 | | | | | 215 | | | | | | | | | |